(12) United States Patent
Levinson

(10) Patent No.: US 11,351,022 B2
(45) Date of Patent: Jun. 7, 2022

(54) IMPLANTABLE MESH AND METHOD OF USE

(71) Applicant: Duke University, Durham, NC (US)

(72) Inventor: Howard Levinson, Durham, NC (US)

(73) Assignee: Duke University, Durham, NC (US)

( * ) Notice: Subject to any disclaimer, the term of this patent is extended or adjusted under 35 U.S.C. 154(b) by 332 days.

(21) Appl. No.: 16/688,600

(22) Filed: Nov. 19, 2019

(65) Prior Publication Data

US 2020/0121438 A1 Apr. 23, 2020

Related U.S. Application Data

(63) Continuation of application No. 15/508,545, filed as application No. PCT/US2015/048557 on Sep. 4, 2015, now Pat. No. 10,500,031.

(60) Provisional application No. 62/105,927, filed on Jan. 21, 2015, provisional application No. 62/091,798, filed on Dec. 15, 2014, provisional application No. 62/045,718, filed on Sep. 4, 2014.

(51) Int. Cl.
*A61F 2/00* (2006.01)
*A61F 2/12* (2006.01)

(52) U.S. Cl.
CPC .............. *A61F 2/0063* (2013.01); *A61F 2/12* (2013.01); *A61F 2002/0068* (2013.01); *A61F 2220/0008* (2013.01); *A61F 2220/0016* (2013.01)

(58) Field of Classification Search
CPC .... A61F 2/0036; A61F 2/0045; A61F 2/0063; A61F 2/12; A61F 2002/0068
See application file for complete search history.

(56) References Cited

U.S. PATENT DOCUMENTS

| 8,585,579 | B2 | 11/2013 | Moschel et al. |
| 2001/0042388 | A1 | 11/2001 | West et al. |
| 2004/0039453 | A1 | 2/2004 | Anderson et al. |
| 2005/0101834 | A1 | 5/2005 | Merade |

(Continued)

FOREIGN PATENT DOCUMENTS

| EP | 1 172 785 | 1/2002 |
| EP | 2002800 | 12/2008 |

(Continued)

OTHER PUBLICATIONS

Office Action dated May 8, 2020 in corresponding Singapore patent application 11201701657V.

(Continued)

*Primary Examiner* — Thaddeus B Cox
(74) *Attorney, Agent, or Firm* — Andrus Intellectual Property Law, LLP

(57) ABSTRACT

An implantable mesh for use in high tension tissue reconstruction includes a mesh body having a surrounding edge and at least two mesh extensions comprised of mesh and extending from the surrounding edge of the mesh body. Each mesh extension has a first end, a second end, and a length therebetween, the first end being integrated into or part of the mesh body. Each mesh extension is configured to be passed through tissue surrounding a reconstruction site to create multiple anchor points with the surrounding tissue upon implantation so as to resist high tension across the reconstruction site without dehiscing or migrating.

23 Claims, 5 Drawing Sheets

(56) References Cited

U.S. PATENT DOCUMENTS

| | | | |
|---|---|---|---|
| 2007/0021649 A1* | 1/2007 | Nowlin | A61F 2/0045 600/30 |
| 2009/0192347 A1* | 7/2009 | Davila | A61B 17/06109 600/37 |
| 2010/0197999 A1 | 8/2010 | Deegan et al. | |
| 2011/0130774 A1 | 6/2011 | Criscuolo et al. | |
| 2012/0004501 A1 | 1/2012 | Beyer | |
| 2013/0317623 A1 | 11/2013 | Trabucco et al. | |
| 2014/0236197 A1 | 8/2014 | Bell et al. | |
| 2016/0030148 A1* | 2/2016 | Cossa | A61F 2/0063 606/151 |

FOREIGN PATENT DOCUMENTS

| | | |
|---|---|---|
| WO | 2012033996 | 2/2012 |
| WO | 2012122215 | 9/2012 |
| WO | 2014067608 | 5/2014 |

OTHER PUBLICATIONS

Office Action dated May 18, 2020 in corresponding European patent application 15838538.5.

Office Action dated Mar. 9, 2020 in corresponding Japan patent application 2017-512911.

* cited by examiner ature, nor is it
intended to be used as an aid in limiting the scope of the
claimed subject matter.

In one embodiment, an implantable mesh for use in
reconstructing tissue includes a mesh body having a surrounding edge and one or more mesh extensions extending
from the surrounding edge of the mesh body. Each mesh
extension has a first end and a second end. The first end is
integrated into or part of the mesh body, and a fixation
device is at the second end.

In another embodiment, an implantable mesh for use in
reconstructing tissue includes a mesh body and one or more
extensions extending from the mesh body. Each mesh extension has a first end and a second end, wherein the first end
of the mesh extension is integrated into or part of the mesh
body. Each mesh extension is configured to permit multiple
anchor points with surrounding tissue upon implantation.

In another aspect, methods of using the claimed implantable mesh in reconstructing tissue or repairing a tissue defect
includes positioning the implantable mesh such that the
mesh body extends across the tissue defect or tissue to be
reconstructed. The method further comprises affixing the
implantable mesh to surrounding tissue by anchoring each
mesh extension to multiple anchor points in the surrounding
tissue.

IMPLANTABLE MESH AND METHOD OF USE

CROSS REFERENCE TO RELATED APPLICATIONS

This patent application is a divisional of U.S. patent application Ser. No. 15/508,545, filed on Mar. 3, 2017, now U.S. Pat. No. 10,500,301, which is a National Phase of PCT/US2015/048557, filed on Sep. 4, 2015, which claims the benefit of priority of U.S. Provisional Patent Application Nos. 62/045,718, filed Sep. 4, 2014; 62/091,798, filed Dec. 15, 2014; and 62/105,927, filed Jan. 21, 2015, all of which are incorporated herein by reference in their entireties.

FIELD

The present disclosure relates to a device and method of use for reconstructing and/or repairing tissue, such as a hernia repair, intended to reduce the likelihood of tissue failure. More specifically, this disclosure relates to an implantable mesh, and a method of implantation therefore, that distributes tensile stress over a larger area between the implantable mesh and the surrounding tissue and, thereby, provides increased durability and better surgical outcomes for patients compared to currently-available devices and methods.

BACKGROUND

Mesh implants are used in many applications to repair or restructure tissue, such as, but not limited to, skin, fat, fascia, or muscle. One common application for such mesh implants is in hernia repair, such as abdominal wall hernia repairs. A hernia is a protrusion of an organ or tissue through an opening or weakness in the walls that normally retain the organ or tissue within a confined space. Most commonly, hernias occur in the abdominal region; however, hernias may occur in many locations throughout the body, including but not limited to the head, thorax/chest, pelvis, groin, axilla, and upper and lower extremities. Hernia is one of the most common surgical pathologies. Approximately 4 million laparotomies are performed in the United States annually, and 2%-30% of them result in incisional hernias. It is estimated that approximately 20 million inguinal hernia operations are performed globally every year, and there are millions more incisional, ventral, and other types of hernias repaired. Traditionally, there are three main approaches to surgical hernia repairs: open, laparoscopic, and robotic hernioplasty. In all three types of repairs, the repaired tissue is reinforced by applying a mesh implant, which may be comprised of synthetic or biologic materials.

Hernias have a tendency to reoccur, and recurrence rates in open surgery have been reported to range from 15-25%. Current recommendations for hernia repair include the use of mesh implants because patients who undergo hernia repair without mesh experience a three-fold increase in recurrence rates compared to patients who undergo hernia repair with a mesh implant.

SUMMARY

This Summary is provided to introduce a selection of concepts that are further described below in the Detailed Description. This Summary is not intended to identify key or essential fe

BRIEF DESCRIPTION OF THE DRAWINGS

The present disclosure is described with reference to the following Figures. The same numbers are used throughout the Figures to reference like features and like components.

DETAILED DESCRIPTION

In the present description, certain terms have been used for brevity, clarity and understanding. No unnecessary limitations are to be inferred therefrom beyond the requirement of the prior art because such terms are used for descriptive purposes only and are intended to be broadly construed.

Figure 1A:
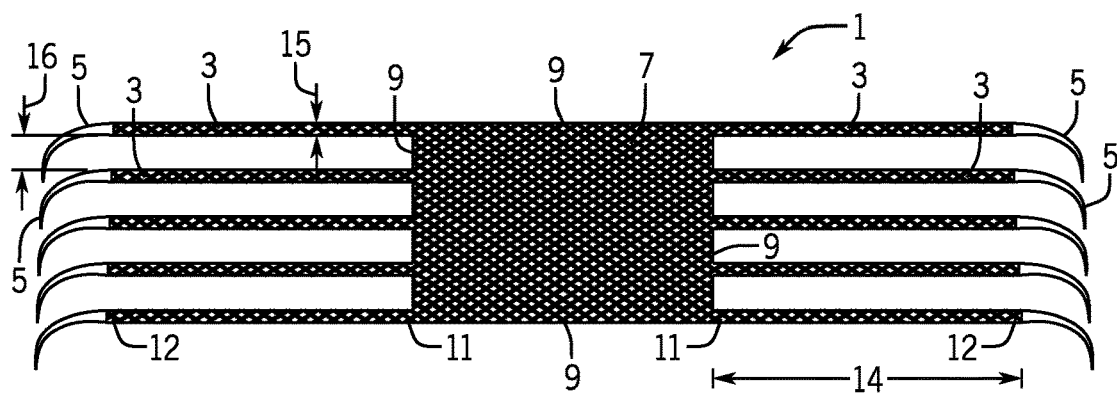
FIG. 1A provides an exemplary embodiment of an implantable mesh according to the present disclosure.

FIG. 1A depicts one embodiment of an implantable mesh 1 having a mesh body 7 and multiple mesh extensions 3 extending from opposing sides of the mesh body 7. At the end of each mesh extension 3 is a fixation device 5, which in the depicted embodiment is a surgical needle. Each mesh extension 3 has a first end 11 that is part of and extends from the mesh body 7. Each mesh extension 3 also has a second end 12 that attaches to the fixation device 5. Each mesh extension 3 has a length 14 between the first end 11 and the second end 12 and a width 15.

The mesh body 7 has a surrounding edge 9 from which the mesh extensions 3 extend. At least two mesh extensions 3 extend from the mesh body 7, and, in various embodiments, the implantable mesh 1 may have any number of additional mesh extensions 3. In the embodiment of FIG. 1A, the implantable mesh 1 has ten mesh extensions 3 arranged in opposing pairs extending oppositely from surrounding edges 9 of the mesh body 7. In FIG. 1A, the mesh extensions 3 extend from only two of the surrounding edges 9. The mesh extensions 3 may extend from more than two or even all of the surrounding edges 9. The mesh extensions 3 are separated by spacing 16 between each mesh extension 3. As depicted, the mesh extensions 3 may be evenly spaced such that the spacing 16 between each mesh extension 3 is equal. In other embodiments, the mesh extensions 3 may be arranged with varied spacing 16 therebetween. For example, certain portions of the surrounding edge 9 may have more mesh extensions 3 that are closer together than at other portions of the surrounding edge of the implantable mesh 1.

The mesh extensions 3 of the implantable mesh 1 have sufficient length 14 to permit multiple anchor points with surrounding tissue upon implantation. An anchor point is a position where the mesh extension passes through some portion of the surrounding tissue in order to provide a force against migration or dehiscence. Multiple anchor points refers to more than one anchor point. For example, each mesh extension 3 may be passed through the surrounding tissue multiple times, such as by weaving or sewing the mesh extensions 3 into the tissue with the fixation device 5. Additionally, in some embodiments the distal end 12 of the mesh extension 3 may be secured to bone. Thereby, the implantable mesh 1 of the present disclosure is configured such that, upon implantation, it can withstand substantial forces, including tensile stress, without failure. This device and method of use is especially applicable for providing a durable reconstruction or repair of a tissue defect, such as a repair of an abdominal hernia or a breast reconstruction.

For example, in standard of care hernia/tissue repair with mesh, the mesh is typically secured to tissue using fixation devices, such as sutures or tacks. With increased intra-abdominal pressure, abdominal wall muscle contraction (e.g. the external oblique, internal oblique, or transversalis muscles), or other externally or internally applied forces, tensile stress is placed on the mesh, fixation device, and tissue at each point where the mesh is secured to the tissue. When tensile stress exceeds tensile strength of any of the mesh, fixation device, or tissue, failure ensues and mesh migration or mesh dehiscence occurs. Tensile Stress ($\sigma$) refers to stress caused by an applied force (F) that acts to elongate a material along the axis of the applied force. Force is distributed over area (A) of material and the anchor points which affix the material to another material. This may be represented by the equation: $\sigma=F/A$. Tensile strength refers to the maximum tensile stress that a material can withstand before yielding, or deforming in shape, and then fracturing or separating in structure, or tearing away (migrating or dehiscing) from another material to which it is affixed at anchor points.

Mesh migration and dehiscence lead to hernia recurrence. Mesh migration refers to movement of a portion of mesh away from one or more anchor points. In one aspect, a portion of the mesh may remain at its original anchor points while another portion of the mesh moves away from one or more anchor points. Dehiscence refers to movement of the entire mesh away from the original anchor points; i.e., none of the mesh remains at its original anchor points. In hernia repair, both mesh migration and dehiscence are frequently caused by tissue failure at the anchor points, and less frequently caused by fixation device failure or mesh failure. Tissue failure is the most common reason for mesh migration or mesh dehiscence because the tensile strength of tissue is significantly less than the tensile strength of the mesh or the fixation device used to attach the mesh to the tissue at anchor points. Tissue failure occurs at anchor points because tensile stress is distributed over a narrow area of tissue and the tensile stress exceeds the tensile strength of the tissue.

Through experience and research in the relevant field, the present inventor has recognized these problems related to mesh migration or dehiscence and the need for a device and method to avoid tissue failure at anchor points by increasing the area over which tensile stress is distributed to the surrounding tissue. In effect, the mesh implant 1 and associated method of implantation reduces the tensile stresses applied to the anchor points to amounts that are less than the tensile strength of the tissue at the anchor points. Specifically, the inventor has developed the presently disclosed implantable mesh 1 to avoid failure at the mesh-tissue interface, enabling the mesh to remain anchored into the tissue and withstand forces which would cause prior art mesh devices to move or be pulled from the surrounding tissue, such as the abdominal wall, due to intra-abdominal pressure, muscular pull or other such external or internally applied forces. For example, the present inventor has recognized that anchor points of an implantable mesh should be able to withstand a tensile stress of at least 16 newtons (N)/centimeter (cm), or greater, because 16 N/cm is approximately the maximum physiologic abdominal stress a human can generate. In other embodiments, the presently disclosed implantable mesh 1 implanted in a patient is able to withstand a range of forces of at least 16 N/cm, at least 24 N/cm, at least 28 N/cm, at least 30 N/com, at least 40 N/cm, or at least 48 N/cm without migrating or dehiscing. In another embodiment, the implantable mesh 1 implanted in a patient is able to withstand a range of forces equal to or greater than 100 N/cm without migrating or dehiscing. In one aspect, the invention achieves this goal by elongating the area of anchor points and by having multiple anchor points of contact between the mesh extensions and surrounding tissue.

The presently disclosed implantable mesh 1 implanted in a patient is able to withstand the range of forces described above within a short time after implantation of the implantable mesh. For example, the implantable mesh 1 can withstand such forces immediately after implantation, within one week, two weeks, three weeks, four weeks, six weeks, two months, three months, four months, or five months after implantation. Some mesh implants are dependent upon tissue ingrowth into the mesh or the anchor points to allow for greater tensile strength and to avoid migration or dehiscence of the implant. These mesh implants are prone to acute failure. The implantable mesh provided herein is immediately woven into the tissue and the fixation strength immediately exceeds the threshold of 16N/cm as shown in the Examples.

By providing multiple anchor points over an elongated area, tensile stress on the tissue and the implant 1 is distributed over a larger area, rather than concentrated at single points of fixation between the mesh and the surrounding tissue, such occurs with suture fixation. Thereby, an implantable mesh 1 implanted according to methods described herein is able to withstand increased tensile stress compared to prior art devices that are sutured to surrounding tissue by conventional anchoring methods. One force distribution mechanism at play is frictional resistance, which is distributed across numerous points of contact between the implantable mesh 1 and the surrounding tissue. The amount of frictional resistance between the implantable mesh 1 and the tissue may depend on numerous factors, including, but not limited to, the area over which the tensile stress is distributed, forces that press the mesh into the tissue, the relative roughness of the mesh and the tissue, the method of fixation, and the extent of bioincorporation of the mesh into the tissue. As long as frictional resistance exceeds tensile stress at each of the anchor points, or points of contact, the mesh will not migrate or dehisce.

In an exemplary embodiment, the length 14 of the mesh extensions 3 is at least 10 cm. In another embodiment, the length 14 of the mesh extensions 3 is at least 16, 18 or 20 cm long and may be up to 25, 30, 35 or 40 cm long; and in still other embodiments the mesh extensions 3 may be even longer than 40 cm to allow for fixation to certain tissues or for the distal end 12 of the mesh extension 3 to be fixed to bone. However, in certain applications, the mesh extensions may be less than 10 cm, such as where the implantable mesh 1 is small and/or intended for repair or reconstruction of tissue that does not withstand significant forces. The mesh extensions 3 of the implantable mesh do not need to all be the same length. In one embodiment, at least one mesh extension is at least 18, 20 or 22 cm long, but the implantable mesh may include additional mesh extensions that are less than 18 cm long or longer than 22 cm long.

Figure 1B:
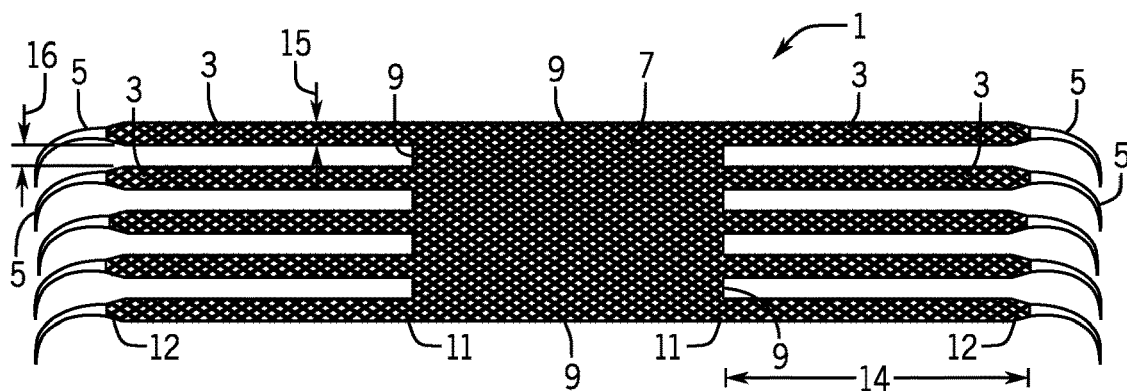
FIG. 1B provides another exemplary embodiment of an implantable mesh according to the present disclosure.

The mesh extensions 3 may have any of various widths. In the embodiment of FIG. 1A, the width 15 of each mesh extension is the same, and the spacing 16 between each mesh extension 3 is wider than the width 15 of each mesh extension. For the embodiment of FIG. 1A, the width 15 of each mesh extension 3 may be between 0.2 cm and 3 cm, or more. For example, experimentation and research by the inventor relating to abdominal hernia repairs has revealed that mesh extensions 3 having a width 15 around 1 cm provide desirable durability results. In the embodiment of FIG. 1A, where the width 15 of each mesh extension 3 is 1 cm, the spacing 16 may be 2 cm or 3 cm, or more. Likewise, in an embodiment where the width 15 of each mesh extension 3 is 3 cm, the spacing 16 may be somewhere between 6 cm and 9 cm, or more. By contrast, the embodiment of FIG. 1B is configured such that the width 15 of each mesh extension 3 is approximately the same as the spacing 16 between each mesh extension 3. In an exemplary embodiment, the width 15 of each mesh extension 3 is between 0.2 cm and 3 cm, and the spacing 16 is the same. For example, in one preferred embodiment, the width 15 of each mesh extension 3 is 1 cm-2 cm, and the spacing 16 between each mesh extension 3 is also 1 cm-2 cm. However, other widths 15 and spacings 16 are contemplated as within the scope of disclosure, and one of skill in the art will appreciate that various dimensions and configurations may be appropriate depending on the tissue defect or reconstruction and surgical approach by which the implantable mesh 1 will be applied. Further, it will be understood by one of skill in the art that any two values listed herein may be combined to provide value ranges for lengths or widths of portions of the implantable mesh, including the mesh extensions 3.

The length 14 of the mesh extensions 3 may also be related to the width 15 of the mesh extensions 3 and the tissue in which the implantable mesh is to be inserted. It is expected that mesh extensions having narrow widths may be capable of being passed through the surrounding tissue at least two times using a shorter length mesh extension. For example, if the mesh extension is 0.5 cm wide, the mesh extension may only need to be 10 cm long to allow at least two passes through the surrounding tissue or to provide two anchor points per mesh extension. In another embodiment, the mesh extensions 3 may be 2 cm wide and 30 cm long to allow adequate anchor points after implantation.

In FIGS. 1A and 1B, the implantable mesh 1 is depicted as including ten mesh extensions 3 with five mesh extensions extending from the surrounding edge 9 on opposite sides of the mesh body 7. As noted above, the mesh extensions 3 may extend from one or more of the surrounding edges 9 of the mesh body 7. In addition, various embodiments may include various numbers of mesh extensions 3. For example, the implantable mesh may include two, three, four, five, six, seven, ten, twelve, fourteen or even more mesh extensions. The number of mesh extensions required may depend on characteristics known to those skilled in the art such as the size and placement of the tissue defect or reconstruction site and the availability or proximity of the surrounding tissue to the tissue defect or site of reconstruction. Having fewer mesh extensions while maintaining or reducing the risk of mesh migration or dehiscence as compared to the standard of care may be advantageous for various reasons. For example, fewer mesh extensions may decrease manufacturing and packaging costs. In addition, as noted in the Examples the amount of time required for implantation is related to the number of mesh extensions and the number of times the mesh extension is passed through the tissue. Reducing the number of mesh extensions may decrease the length or complexity of the surgery or result in decreased damage and concomitant pain for the patient recipient of the implantable mesh.

As depicted in FIGS. 1A and 1B, the mesh extensions 3 may be of uniform mesh construction with the mesh body 7. In such an embodiment, the mesh extensions 3 and the mesh body 7 may be comprised of the same set of mesh threads 8 woven or knitted together to form a continuous mesh pattern. In general, the mesh is an arrangement of biocompatible threads that form a flexible material, for example a knitted material, woven material, a non-woven material, or a braided material. For example, the mesh may be of an openwork structure or pattern, i.e. having pores to encourage tissue in-growth. Such a mesh may be bioabsorbable, partly bioabsorbable or permanent. The organization of the mesh fibers 8 (in knitted material, woven material, braided material, etc.) or surface structure (e.g., in non-woven material) in the mesh extensions 3 may be controlled by methods known in the art to optimize the biomechanical properties, such as tensile strength, as well as for porosity, morphology, and geometry as they relate to tensile strength and bioincorporation, which also influences tensile strength and frictional resistance. Various knitting techniques known in the art may be used to create the mesh of the implantable mesh 1. These include, but are not limited to, warp knitting, weft knitting, and circular knitting. Alternatively or additionally, various weaving techniques known in the art may be used to create the mesh of the implantable mesh 1. These include, but are not limited to, hexagonal open stitching (e.g., PARIETINE® mesh), interlocking fiber junctions (e.g., PROLENE® mesh, SURGIPRO Pro® mesh), diamond shape open stitching (e.g., ULTRAPRO® mesh), 2-dimensional weaves, and 3-dimensional weaves.

The mesh threads 8 may be, for example, monofilaments, braided, or a combination of monofilament and braided. Further, the mesh threads 8 may be coated to enhance tensile strength, frictional resistance, and bioincorporation. The mesh may be comprised of any biocompatible material that has the properties (e.g. tensile strength, durability, etc.) to withstand the forces described herein when implanted in tissue. In some embodiments the mesh comprises a synthetic mesh, which is a mesh made from biocompatible and synthetic materials, including, but not limited to, polypropylene, polyethylene terephthalate polyester, expanded polytetrafluroethylene (ePTFE), polyglactin, polyglycolic acid, trimethylene carbonate, poly-4-hydroxybutyrate (P4HB), polyglycolide, polylactide, and trimethylene carbonate (TMC). In other embodiments, the mesh comprises a biological mesh, which is a mesh made from biocompatible and biological materials, including, but not limited to, human dermis, porcine dermis, porcine intestine, bovine dermis, and bovine pericardium. The mesh may also be a comprised of a combination of synthetic and biologic materials.

Figure 2:
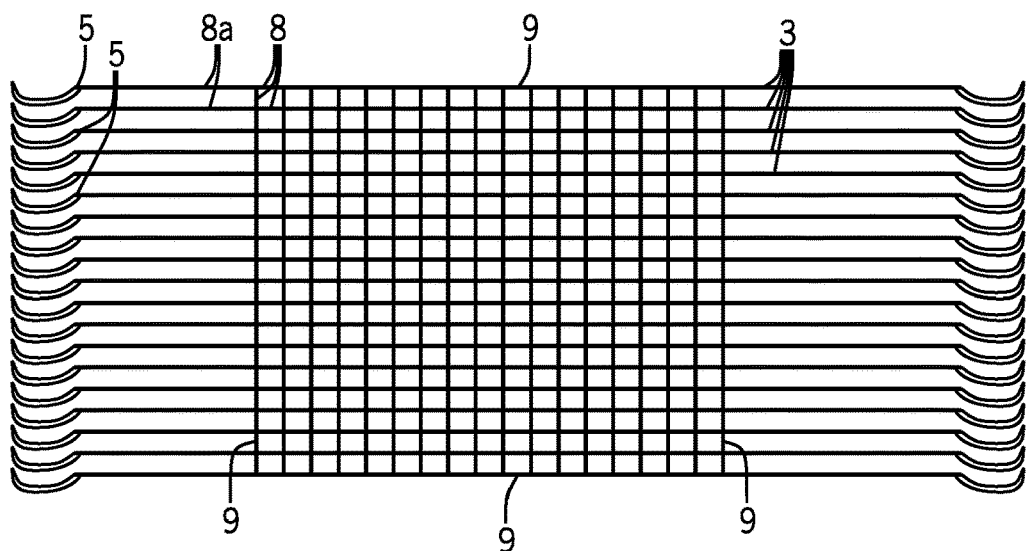
FIG. 2 schematically depicts another exemplary embodiment of an implantable mesh according to the present disclosure.
Figure 3:
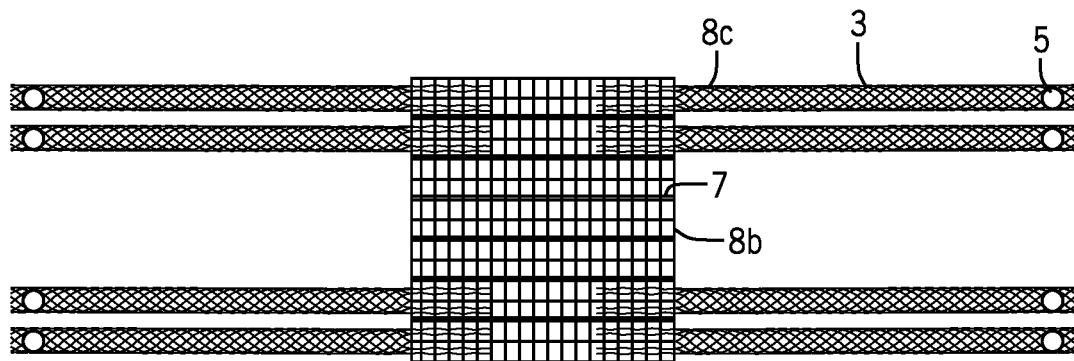
FIG. 3 schematically depicts another exemplary embodiment of an implantable mesh according to the present disclosure.
Figure 4:
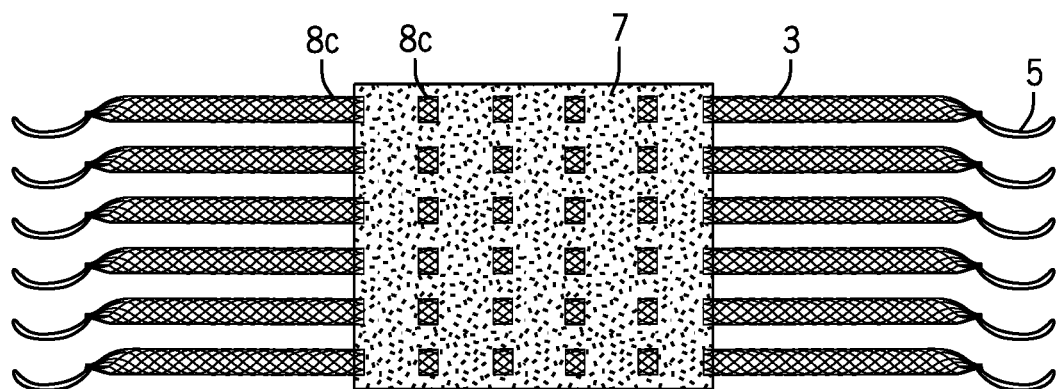
FIG. 4 schematically depicts yet another exemplary embodiment of an implantable mesh according to the present disclosure.

In another embodiment, the mesh extensions 3 are formed of a different construction. In the embodiment of FIG. 2, the mesh extensions 3 are formed by ends 8a of the mesh threads 8. For example, one or both ends of the threads 8 woven or knitted together to form the mesh body 7 may extend outward from the mesh body 7 to form the mesh extensions 3. FIGS. 3 and 4 depict another embodiment where the mesh extensions 3 are comprised of mesh threads 8c woven or knitted together separately from the mesh threads 8b of the mesh body 7. The mesh threads 8c at the first end 11 of the mesh extensions 3 are then integrated into the mesh body 7, such as woven into the mesh body 7.

Like the mesh threads 8b of the mesh body 7, the mesh threads 8c of the mesh extensions 3 may be woven together in any pattern, including any of those referenced hereinabove. In the example depicted in FIG. 3, the mesh extensions are comprised of mesh threads 8c twisted into helixes. The number of mesh threads 8c forming the helix for each exemplary mesh extension 3 may vary to allow for different thicknesses. Depending on the tissue to which the device will be fixed, the thickness and length of each of the helical mesh extensions 3 may be different.

The threads 8c of at the first end of each mesh extension 3 may be integrated into the mesh body in various ways. For example, as depicted in FIG. 3, the mesh threads 8c of the mesh extensions are woven into the mesh of the mesh body 7 and extend part way across the mesh body 7. In other embodiments, the mesh threads 8c of the mesh extensions 3 may be woven all the way across the mesh body 7. In still other embodiments, such as that depicted in FIG. 4, the mesh extensions 3 are comprised of mesh threads 8c woven all the way across the device, such that opposing mesh extensions 3 are formed of the same mesh threads 8c. In such an embodiment, the woven mesh threads 8c of the mesh extension 3 are passed through the mesh body 7. The embodiments of FIGS. 3 and 4 may be especially useful where the mesh body 7 and the mesh extensions 3 are not comprised of the same material. For example, in the embodiment of FIG. 4, the mesh body 7 may be comprised of biologic material, and the mesh extensions 3 may be comprised of synthetic material, or vice versa. Exemplarily, the mesh threads 8c of the mesh extensions 3 may be, for example, polypropylene threads woven together in a helical pattern. The helical woven mesh extensions 3 may then be woven through a mesh body 7, which may be comprised of a biological material described and listed above.

The implantable mesh 1 may be produced from one layer of mesh material, or from a plurality of layers of mesh materials, which may be the same or different materials arranged in the same or different construction. Additionally, the implantable mesh 1 may be any shape or configuration that provides a mesh body and at least two mesh extensions extending therefrom. In some embodiments, the mesh body 7 may be circular, oval, rectangular, square, triangular, or any other multi-sided shape. Additionally, the mesh extensions 3 may vary in shape and dimension.

Various fixation devices 5 may be at the second end 12 of each mesh extension 3. The fixation devices 5 may be any element or series of elements that enable fixation of the mesh extension to the tissue. Exemplary fixation devices include, but are not limited to, surgical needles, staples, tacks, screws, laser-assisted tissue welding, fibrin sealant, glue, salute "Q" ring, Mitek anchors, and/or sutures. Each fixation device 5 may be permanently or removably attached to the second end 12 of each mesh extension 3. Alternatively or additionally, the fixation device 5 may be permanently or removably attached to some other portion of each mesh extension 3. Moreover, the fixation device 5 may be an element that is permanently implanted in the patient, or is removed from the implantable mesh 1 once it is implanted in the patient.

In the examples of Figures of 1A, 1B, 2, and 4, the fixation devices 5 are surgical needles. In those embodiments, the surgical needles are there to assist in affixing the mesh extensions 3 into the surrounding tissue—i.e. to allow the surgeon to pass the mesh extensions 3 through the surrounding tissue. In such embodiments, once the mesh extensions 3 have been passed through the surrounding tissue a sufficient number of times, which may be the number of times that the length 14 of the mesh extension 3 will allow in a particular application, the mesh extension 3 may be cut at the second end 12 to remove the surgical needle fixation device 5. FIG. 3 depicts another embodiment where the fixation device 5 is a tack. In one embodiment, the tacks 5 may be attached at the second end 12 of each mesh extension 3 once the mesh extension 3 has been woven into or affixed to the surrounding tissue. In such an embodiment, the tacks 5 may operate to anchor the mesh extensions to the tissue or to surrounding bone. In similar embodiments, multiple tacks may be used at various locations along the mesh extensions 3 to provide multiple additional anchor points. Such an embodiment utilizing tacks may be appropriate, for example, in laparoscopic surgeries and/or in robotic hernia prostheses.

When implanted, the implantable mesh 1 is affixed to the tissue defect or the tissue to be reconstructed and/or the surrounding tissue at multiple anchor points. This may be executed by passing each mesh extension through the surrounding tissue, such as by weaving or knitting (i.e., no sutures) the mesh, mesh extension, fixation device and/or extension means into the tissue (e.g., abdominal fascia). In one embodiment, the implantable mesh 1 is implanted into a patient for reconstructing or repairing a tissue defect, such as a hernia, or a breast reconstruction. The tissue is penetrated at an entry point, such as at the location of a hernia, or at an incision or a surgical separation of tissue. The implantable mesh 1 is then positioned so as to enable reconstruction or repair of the tissue defect. For example, the implantable mesh 1 may be positioned such that the mesh body 7 extends across the tissue defect. The mesh extensions are then anchored to the surrounding tissue at multiple anchor points, such as by weaving or passing the mesh extension 3 into or through the surrounding tissue 30 using one or more of the patterns exemplified in FIGS. 6A-6D, discussed hereinbelow.

Figure 5A:
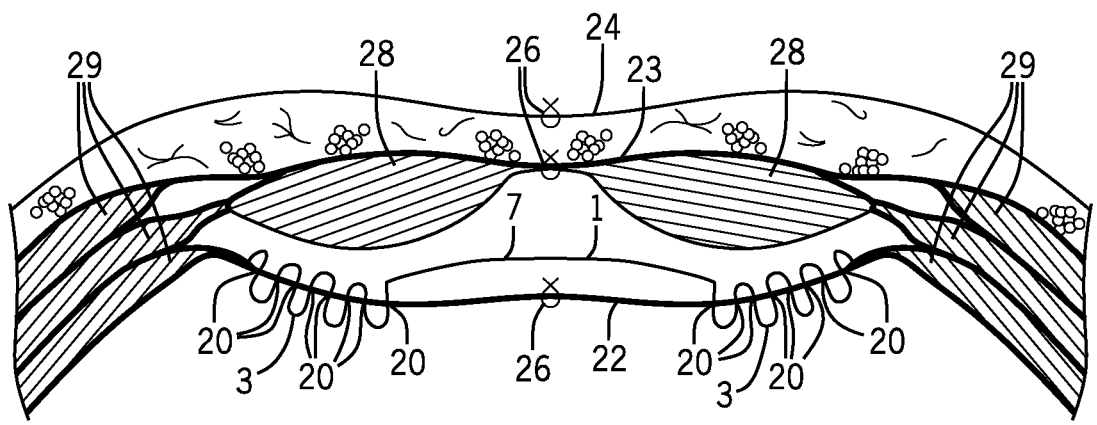
FIGS. 5A and 5B schematically depict an embodiment of an implantable mesh implanted in a patient to repair an abdominal hernia.
Figure 5B:
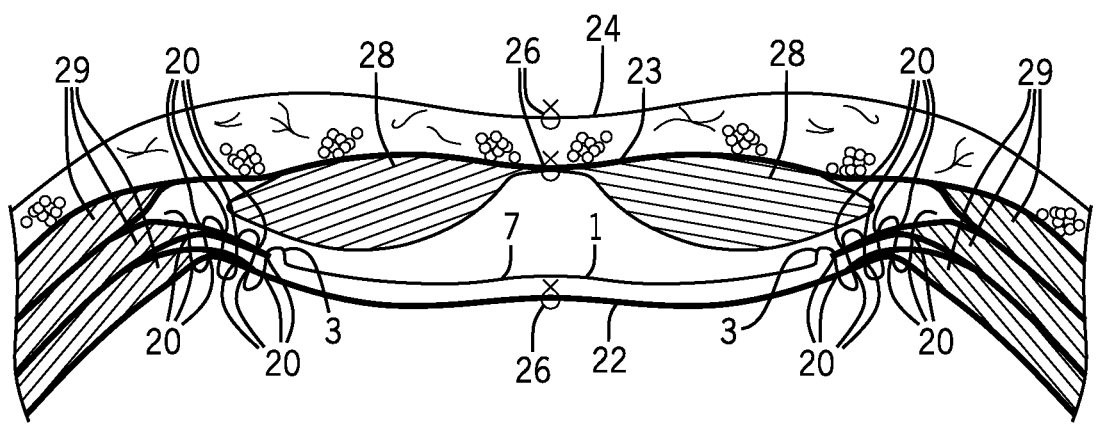

FIGS. 5A and 5B demonstrate an exemplary use of the implantable mesh 1 to repair an abdominal hernia, where each figure depicts the implantable mesh 1 at a possible location for repairing a hernia. However, in other embodiments and situations, the implantable mesh 1 may be placed in any one or more of several different anatomic planes, depending on the hernia, the patient's anatomy, the fixation method, surgeon's judgment, etc. In the example of FIGS. 5A and 5B, the implantable mesh 1 is located on the posterior abdominal fascia 22. In other embodiments and implantation methods, the implantable mesh 1 may be located at any number of other locations along the abdominal wall, such as on anterior abdominal wall as an onlay, within the muscle of the abdominal wall as an inlay, below the muscle of the abdominal wall as a sublay, or as an underlay. The mesh may be placed extraperitoneal or intraperitoneal, or in any number of other locations for abdominal hernia repair.

In the examples of FIGS. 5A and 5B, the hernia has occurred between the rectus abdominis muscles 28. In such an embodiment, an incision may be made in the skin 24 so that the herniated area may be accessed. The herniated area between the rectus abdominis muscles 28 may be penetrated, and any tear or separation of the posterior abdominal fascia may be repaired with sutures 26. The implantable mesh 1 is then placed such that the mesh body 7 extends across the herniated area. The mesh extensions 3 are then passed through tissue surrounding the hernia, such as by weaving the mesh extensions 3 into the surrounding tissue. In the example of FIG. 5A, the implantable mesh 1 overlays the posterior abdominal fascia and below the rectus muscles. The mesh extensions 3 are woven into the posterior abdominal fascia 22 to form multiple anchor points 20 with the surrounding tissue in order to provide a force against mesh migration or dehiscence and to protect the primary repair of the midline fascia. In the embodiment of FIG. 5B, the mesh extensions 3 are affixed more laterally than in FIG. 5A and include passes through the oblique muscles 29 and their fascia.

Once the implantable mesh 1 is affixed to the surrounding tissue, the tissue above the implantable mesh 1 may be closed with sutures 26. In the exemplary situation depicted in FIGS. 5A and 5B, sutures 26 are placed to close the anterior fascia 23 of the rectus abdominis muscle 28, and then also to close the skin 24. Implanted in this exemplary fashion, the implantable mesh 1 will remain in place and not migrate or dehisce because the mesh extensions 3 are arranged to have multiple anchor points 20 throughout the surrounding tissue 30 so as to distribute forces over a large area of tissue and prevent tissue failure.

In another embodiment of a method of use, the implantable mesh 1 is utilized to reconstruct breast tissue by anchoring the device to the breast tissue, chest wall, or rib bone. Currently, synthetic and biologic meshes are used in breast reconstruction surgery in an attempt to solve the problem of implant malposition or of the implant pushing against the skin envelope and causing the wound to open, the breast to deform, or the skin to become thinned-out. However, due to tissue failure, standard mesh fixation methods are often ineffective in holding the mesh to the pectoral muscle and/or the ribs. The presently disclosed implantable mesh 1 and corresponding method of implantation provides an effective solution to these problems presented in reconstructing breasts because, as described thoroughly above, they allow multiple fixation points and provide greater tissue fixation compared to sutures. Also, the mesh may function as a scaffold helping native tissue in-growth. Moreover, in certain embodiments and implantation methods, the mesh extensions 3 may be of sufficient length that they may be fixed or connected to the ribs, such as by stapling, tacking, or tying the mesh extensions 3 to the ribs.

Figure 6A:
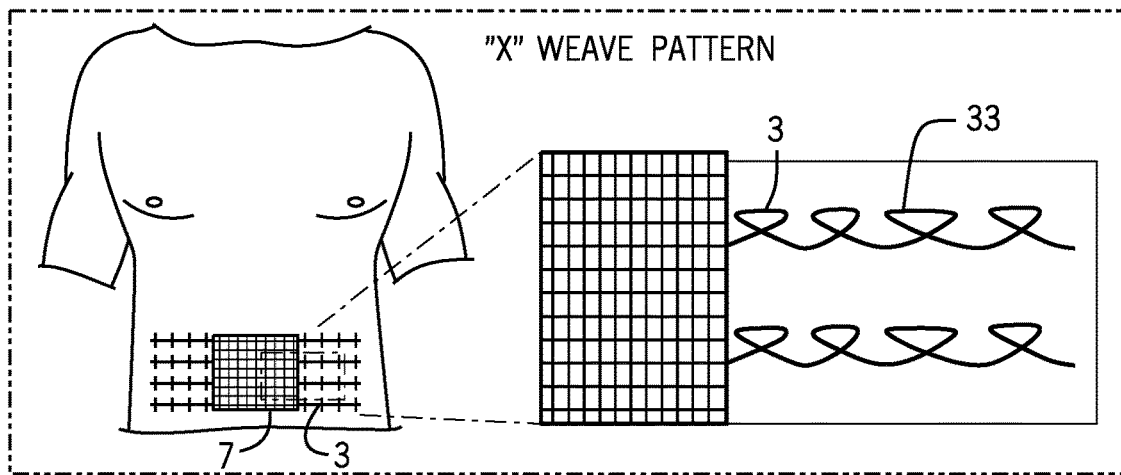
FIGS. 6A-6D depict various embodiments of weave patterns for affixing an implantable mesh to surrounding tissue.
Figure 6B:
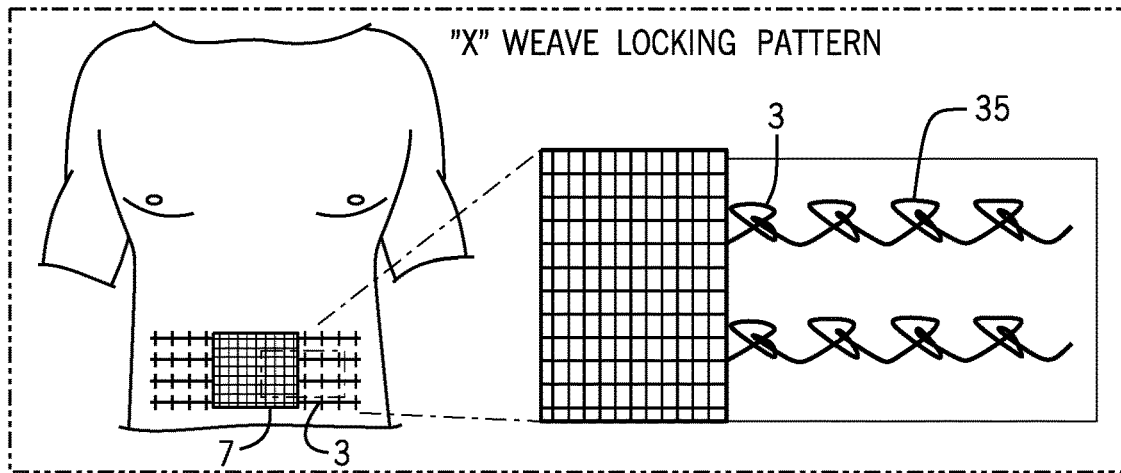
Figure 6C:
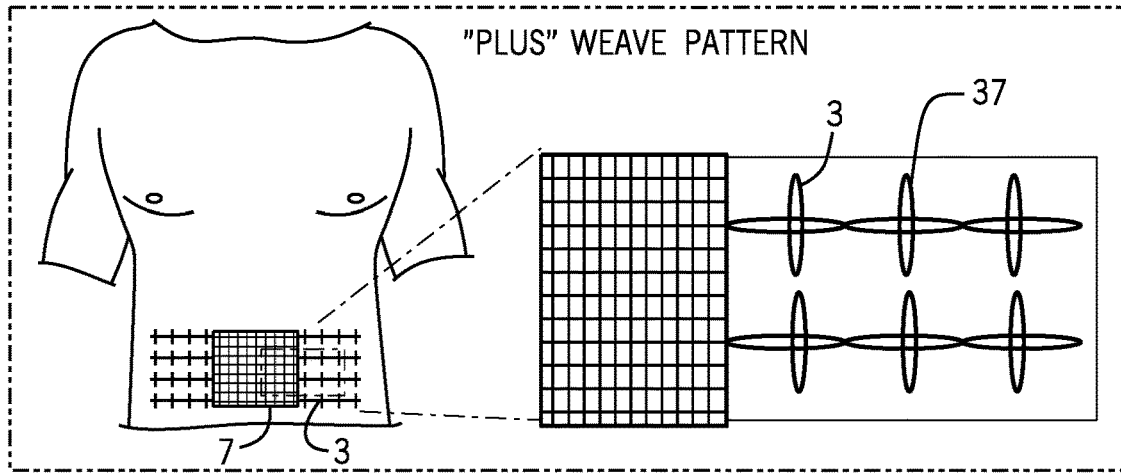
Figure 6D:
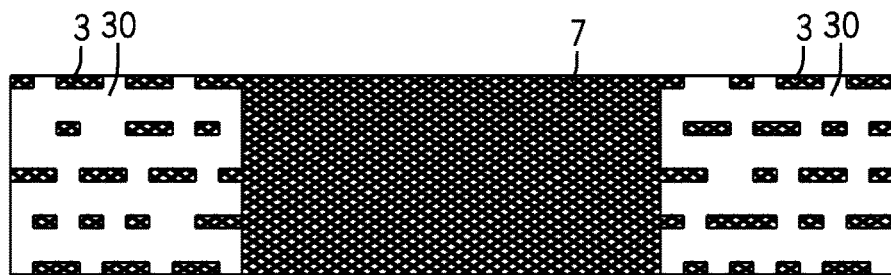

The patterns for affixing the device to the surrounding tissue may vary widely, including, but not limited to, a locking x-weave pattern, an x-weave pattern, or a plus weave pattern, as per the surgeon's expertise. FIGS. 6A-6D exemplify various weave patterns that may be used to affix the implantable mesh 1 to tissue 30. FIG. 6A exemplifies an embodiment with the mesh extensions 3 woven into surrounding tissue 30 in an x-weave pattern. FIG. 6B exemplifies an embodiment with the mesh extensions 3 woven into surrounding tissue 30 in a locking x-weave pattern. FIG. 6C exemplifies an embodiment with the mesh extensions 3 woven into surrounding tissue 30 in a plus weave pattern. FIG. 6D exemplifies an embodiment with the mesh extensions 3 woven into surrounding tissue 30 in a longitudinal weave pattern. FIG. 6D also demonstrates a varied longitudinal weave pattern, where the length of the weave stitches and the anchor point locations are varied between adjacent mesh extensions 3 so as to avoid concentrating forces, such as tensile stress, on certain areas of tissue 30. The extensions may also be woven into tissue at a point remote from the primary hernia repair, where tissue integrity is superior. For example, select patients will often have compromised fascia from circumstances such as but not limited to previous surgeries or from their body habitus (e.g., morbid obesity) or from their disease states or from medicants like steroids.

Thereby, the forces may be dispersed and evenly distributed across a larger area of tissue 30. As the extensions are secured to the surrounding tissue, one or more knots of the mesh extensions 3 to the surrounding tissue 30 may also be formed, which may vary in their configuration to enhance fixation to the tissue 30. In some embodiments of implantation methods, one or more sutures may also be used to further secure the mesh extensions 3 to the surrounding tissue 30. For example, sutures may be used to tie a knot around the extension, similar to how Pulver-Taft weaves are secured in tendon repair.

Figure 7:
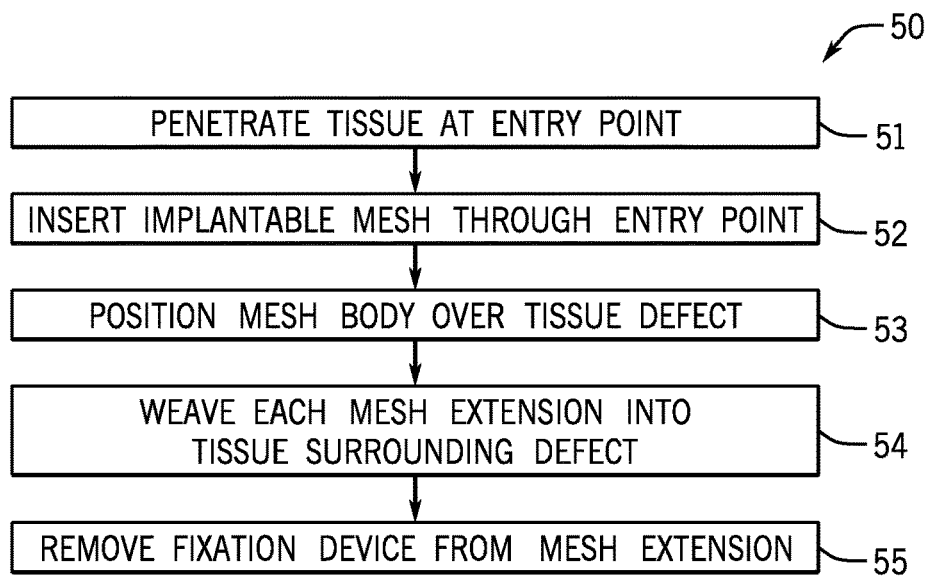
FIG. 7 is a flowchart depicting one embodiment of a method of using the implantable mesh of the present disclosure in reconstructing or repairing a tissue defect.

FIG. 7 presents a flow chart exemplifying one method 50 of using the implantable mesh 1 in reconstructing or repairing a tissue defect. First, the tissue is penetrated at an entry point at step 51. The implantable mesh 1 is then inserted through the entry point at step 52, and the mesh body 7 is positioned across the tissue defect at step 53. The mesh extensions 3 are then woven into the surrounding tissue, such as by using a surgical needle fixation device 5 attached to distal end of each mesh extension 3. At step 55, the surgical needle fixation device 5 may then be removed from each mesh extension 3, for example by cutting the end 12 of each mesh extension 3.

Figure 8:
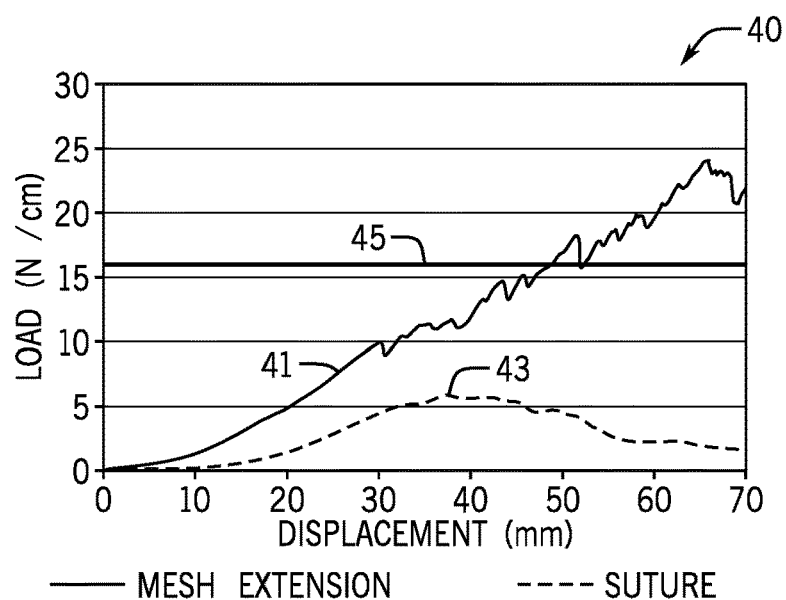
FIG. 8 is a graph depicting the load-bearing capabilities of the implantable mesh of the present disclosure as compared to a prior art device and method.

FIG. 8 provides a graph comparing the load-bearing capabilities of the implantable mesh 1 and the current standard of care mesh fixation method using sutures. Line 41 of the graph demonstrates the load versus displacement of the implantable mesh 1 when affixed to the abdominal fascia according to some embodiments of the present disclosure. Line 43 of the graph demonstrates the load versus displacement of a standard hernia mesh affixed to the abdominal fascia using current standard of care suturing techniques. The graph demonstrates that the implantable mesh device 1, implanted using the methods disclosed herein, provides far superior stress shielding of the tissue (i.e., lowering the tensile stress on the tissue at anchor points below the tensile strength of the tissue). As described above, the present inventor has recognized that a implantable mesh 1 should be able to withstand a tensile stress of at least 16 N/cm without migrating or dehiscing. Line 45 marks this minimum load requirement. As the graph demonstrates, the current standard of care mesh fixation provides a maximum load-bearing strength of just over 5 N/cm, which is significantly less than this minimum requirement of 16 N/cm. The embodiment of the implantable mesh 1, on the other hand, provides load-bearing strength that well-exceeds the exemplary minimum requirement of 16 N/cm.

The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

The following examples are meant only to be illustrative and are not meant as limitations on the scope of the invention or of the appended claims.

EXAMPLES

Bench top studies were conducted comparing the standard of care mesh implant and fixation method to the implantable mesh 1 and implantation method disclosed and described herein. Human abdominal tissue 30 was modeled in hemi-dumbbell shaped porcine abdominal wall segments sized at 12 cm×10 cm×0.5 cm. For the standard of care device and fixation method, Ethicon Ultrapro Monocryl Prolene Composite mesh was anchored to the hemi-dumbbell swine specimen with four discrete 0 polypropylene sutures at 1 cm intervals. The sutures were fixed at the third pore from the edge of the mesh. To model the implantable mesh 1, an Ethicon Ultrapro Monocryl Prolene Composite mesh was cut with a scissor to model a mesh body 7 with mesh extensions 3 measuring 1 cm in width and 30 cm in length. The mesh extensions 3 were woven into the hemi-dumbbell swine specimen using four running locking stitch patterns, and no sutures or knots were used. The opposing edge of the mesh on both samples was gripped with an instron. The two sides were then distracted at 100 mm per minute until the mesh completely dehisced from the tissue and/or total tissue failure was achieved. Load and displacement data were acquired at a sample rate of 100 hz. Force displacement was obtained and converted to stress displacement to interpret UTS. The UTS was recorded as N/cm, where N was the force applied until failure and cm was the outermost distance between the furthest apart mesh extensions.

The standard of care fixation method and device, using the four discrete 0 Surgipro polypropylene sutures, dehisced from the tissue 30 at about 30 N total force as the sutures pulled out of the tissue and remained attached to the mesh. The tissue generally failed at or near the four anchor points created by the four discrete 0 Surgipro polypropylene sutures. This is significantly less than the force tolerated by the sample using the mesh implant 1 affixed according to the methods disclosed herein. The implantable mesh 1 with the mesh extensions 3 woven into the tissue 30 using four running locking stitch patterns did not dehisce from the tissue until about 121 N total force. The mesh extensions dehisced by gradually slipping out of the tissue 30, rather than by the tissue failing.

Further tests were conducted under similar conditions modifying other variables, including weave pattern, mesh throw count, and interspace distance between each mesh extension. To test which weave pattern provided the most strength, three mesh extensions were woven into one hemi-dumbbell shaped fascia-muscle slab of porcine abdominal wall in pre-determined weave patterns, including a running x weave pattern, locking x weave pattern, a continuous locking pattern and a linear parallel pattern. The standard of care mesh fixation using sutures as describe above was also included. The number of throws was held constant at 4 throws. Following the four throws, the mesh ribbon was anchored to the tissue with a surgeon's knot. Time taken to weave each elongation arm was recorded and averaged for each group. The samples were exposed to increasing tensile stress as described above.

Mode of failure for the standard of care mesh was by anchor point failure. Mode of failure for all woven meshes was remote tissue failure, or failures distal to weave anchor points. The following table provides the data:

|  | UTS (N/cm) | Time to suture mesh extension (s) |
| --- | --- | --- |
| Standard of Care | 12.8 | 18 |
| X-Weave | 33.7 | 63 |
| X-Locking | 29.4 | 71 |
| Continuous Locking | 39.2 | 54 |
| Linear Parallel | 24.8 | 37 |

To test which number of throws provided the most strength, the following test was performed. Three mesh ribbons were woven into one dumbbell shaped fascia-muscle slab of porcine abdominal wall, according to the above-description, using an x-locking weave pattern with each of 2, 3, and 4 throws. The standard of care mesh fixation using sutures as describe above was also included. Each fixation method was tested in triplicate. Interspace distance was held constant at 1 cm. Time taken to weave each ribbon was recorded and averaged for each group. The samples were exposed to increasing tensile stress as described above. Force displacement was obtained and then converted to stress-displacement to interpret ultimate tensile strength (UTS). Mode of failure for the standard of care mesh was by anchor point failure. Mode of failure for all woven meshes was remote tissue failure, or failures distal to weave anchor points. The following table provides the data:

|  | UTS (N/cm) | Time to suture mesh extension (s) |
| --- | --- | --- |
| Standard of Care | 11.2 | 19 |
| 4 throws | 41.8 | 65 |
| 3 throws | 71.4 | 47 |
| 2 throws | 45.0 | 33 |

To test which interspace distance between the mesh extensions provided the most strength, the following test was performed. Two mesh ribbons were woven into one dumbbell shaped fascia-muscle slab of porcine abdominal wall using an x-locking weave pattern. The interspace distance was modified for each sample, including at 1 cm, 2 cm, and 3 cm, and each was tested in triplicate. The number of throws was held constant at three throws. Time taken to weave each ribbon was recorded and averaged for each group. The samples were exposed to increasing tensile stress as described above. Force displacement was obtained and then converted to stress-displacement to interpret UTS. Mode of failure for the standard of care mesh was by anchor point failure. Mode of failure for all woven meshes was remote tissue failure, or failures distal to weave anchor points. The following table provides the data:

|                    | UTS (N/cm) | Time to suture mesh extension (s) |
|--------------------|------------|-----------------------------------|
| Standard of Care   | 13.6       | 18                                |
| 3.0 cm Interspace  | 24.7       | 61                                |
| 2.0 cm Interspace  | 36.1       | 61                                |
| 1.0 cm Interspace  | 31.8       | 61                                |

To test which width of mesh extension provided the most strength, the following test was performed. Two mesh ribbons were woven into one dumbbell shaped fascia-muscle slab of porcine abdominal wall using an x-locking weave pattern. The mesh arm width was modified for each sample, including 1 cm, 1.5 cm, and 2 cm, and each was tested in triplicate. The number of throws was held constant at three throws and interspace distance held constant at 1 cm. Time taken to weave each ribbon was recorded and averaged for each group. The samples were exposed to increasing tensile stress as described above. Force displacement was obtained and then converted to stress-displacement to interpret UTS. Mode of failure for the standard of care mesh was by anchor point failure. Mode of failure for all woven meshes was remote tissue failure, or failures distal to weave anchor points. The following table provides the data:

|                    | UTS (N/cm) | Time to suture mesh extension (s) |
|--------------------|------------|-----------------------------------|
| Standard of Care   | 13.6       | 18                                |
| 3.0 cm Interspace  | 24.7       | 61                                |
| 2.0 cm Interspace  | 36.1       | 61                                |
| 1.0 cm Interspace  | 31.8       | 61                                |

To test whether a single pass through the surrounding tissue would offer sufficient tensile strength, the following test was performed. An Ethicon Ultrapro Monocryl Prolene Composite mesh was cut with a scissor to create mesh extensions measuring 2.0 cm in width and 15.0 cm in length. Two mesh extensions were placed per specimen at 2 cm intervals. As above, hemi-dumbbell shaped porcine abdominal wall segments (14-cm×19-cm×0.5-cm) cut for optimal tensile strength testing capability were used as the specimen. Two small bilateral 2 mm holes were made in each tissue specimen. A mesh extension was pulled through each hole. All variables were compared to Ethicon Ultrapro Monocryl Prolene Composite mesh anchored using simple interrupted 0 polypropylene sutures placed at 1-cm intervals (standard of care). The sutures were passed through the third pore from the edge of the mesh. Tensile strength testing was carried out on an Instron according to ASTM specification D5034. The gauge length (length of material between grips) was 200 mm composing 120 mm of tissue and 80 mm of mesh. The displacement rate was 100 mm/minute. Load and displacement was recorded at a sampling rate of 100 Hz. Force displacement was obtained and converted to stress displacement to interpret UTS. The UTS was recorded as N/cm, where N was the force applied until failure and cm was the outermost distance between the furthest apart mesh extensions.

|                                      | UTS (N/cm) | Time to suture mesh extension (s) |
|--------------------------------------|------------|-----------------------------------|
| Standard of Care                     | 13.6       | 18                                |
| Single Pass 2 cm Mesh Extensions     | 0.60       | 20                                |

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

I claim:

1. An implantable mesh for use in high tension tissue reconstruction, the implantable mesh comprising:
    a mesh body having a surrounding edge;
    at least two mesh extensions comprised of mesh and extending from the surrounding edge of the mesh body, each mesh extension having a first end, a second end, and a length therebetween, the first end being integrated into or part of the mesh body; and
    wherein the mesh body is configured to be positioned in a plane across a reconstruction site and each mesh extension is configured to be passed through tissue surrounding the reconstruction site to create multiple anchor points with the surrounding tissue immediately upon implantation so as to resist high tension in the plane across the reconstruction site and across the mesh body between the at least two extensions without dehiscing or migrating.

2. The implantable mesh of claim 1, wherein the tissue being reconstructed or repaired is one of abdominal tissue, breast tissue, or tendon.

3. The implantable mesh of claim 1, comprising two or more mesh extensions extending from the surrounding edge of the mesh body such that their principal vectors are at obtuse angles to one another.

4. The implantable mesh of claim 3, wherein the two or more mesh extensions are arranged in opposing pairs positioned directly across from one another such that they are configured to resist high tension across the reconstruction site.

5. The implantable mesh of claim 4, further comprising at least four mesh extensions comprised of mesh and arranged in at least two opposing pairs.

6. The implantable mesh of claim 5, wherein a first one of the at least two opposing pairs is aligned along a top edge of the mesh body and a second one of the at least two opposing pairs is aligned along a bottom edge of the mesh body.

7. The implantable mesh of claim 6, further comprising one or more additional mesh extensions extending from the surrounding edge of the mesh body at a location between the top edge and the bottom edge.

8. The implantable mesh of claim 1, wherein all of the at least two mesh extensions are arranged in opposing pairs positioned directly across from one another.

9. The implantable mesh of claim 8, wherein the mesh body is rectangular or square and all of the at least two mesh extensions extend from one of two opposite edges of the mesh body.

10. The implantable mesh of claim 8, further comprising a surgical needle permanently connected to the second end of each of the at least two mesh extensions.

11. The implantable mesh of claim 1, wherein, immediately upon implantation, the implantable mesh is configured to resist tension across the reconstruction site of at least 16 newtons per centimeter without dehiscing or migrating from the reconstruction site.

12. The implantable mesh of claim 11, wherein, immediately upon implantation, the implantable mesh is configured to resist tension across the reconstruction site of at least 32 newtons per extension without dehiscing or migrating from the reconstruction site.

13. The implantable mesh of claim 1, wherein the mesh body and the at least two mesh extensions are fabricated as a continuous mesh construction.

14. The implantable mesh of claim 13, wherein the at least two mesh extensions and the mesh body are comprised of a planar mesh.

15. The implantable mesh of claim 1, wherein the plane across the reconstruction site is an anatomic plane.

16. An implantable mesh for use in high tension tissue reconstruction, the implantable mesh comprising:
a planar mesh forming a mesh body and at least two mesh extensions extending in opposite directions from the mesh body; and
wherein the mesh body is configured to be positioned in a plane across a reconstruction site and each mesh extension is configured to be passed through tissue surrounding the reconstruction site so as to immediately resist high tension in the plane across the reconstruction site and across the mesh body between the at least two extensions without dehiscing or migrating.

17. The implantable mesh of claim 16, wherein all of the at least two mesh extensions extend from one of two opposite edges of the mesh body.

18. The implantable mesh of claim 17, wherein the mesh body is rectangular or square having a top edge, a bottom edge, and two side edges, wherein all of the at least two mesh extensions extend from one of the two side edges of the mesh body.

19. The implantable mesh of claim 17, further comprising at least four mesh extensions comprised of mesh and arranged in at least two opposing pairs, wherein a first one of the at least two opposing pairs is aligned along a top edge of the mesh body and a second one of the at least two opposing pairs is aligned along a bottom edge of the mesh body.

20. The implantable mesh of claim 16, further comprising at least six mesh extensions comprised of mesh and arranged in at least three opposing pairs.

21. The implantable mesh of claim 20, further comprising at least eight mesh extensions comprised of mesh and arranged in at least four opposing pairs.

22. The implantable mesh of claim 16, wherein the plane across the reconstruction site is an anatomic plane.

23. An implantable mesh for use in high tension tissue reconstruction, the implantable mesh comprising:
a mesh body having a surrounding edge;
at least two mesh extensions comprised of mesh and extending from the surrounding edge of the mesh body, each mesh extension having a first end, a second end, and a length therebetween, the first end being integrated into or part of the mesh body; and
wherein each mesh extension is configured to be passed through tissue surrounding a reconstruction site to create multiple anchor points with the surrounding tissue upon implantation so as to immediately resist high tension across the reconstruction site without dehiscing or migrating and without the use of any fixation device securing each extension to the surrounding tissue.

* * * * *